(12) United States Patent
Ahn

(10) Patent No.: US 7,605,910 B2
(45) Date of Patent: Oct. 20, 2009

(54) PARTICLE MEASURING SYSTEM AND METHOD

(76) Inventor: Kang Ho Ahn, 102-1504, Ichon Apartment, 412, Ichon-Dong, Yongsan-Ku, Seoul (KR) 140-030

( * ) Notice: Subject to any disclaimer, the term of this patent is extended or adjusted under 35 U.S.C. 154(b) by 278 days.

(21) Appl. No.: 11/776,298

(22) Filed: Jul. 11, 2007

(65) Prior Publication Data

US 2008/0047373 A1 Feb. 28, 2008

(30) Foreign Application Priority Data

Jul. 12, 2006 (KR) .................. 10-2006-0065286

(51) Int. Cl.
*G01N 1/00* (2006.01)
*G01N 15/02* (2006.01)
(52) U.S. Cl. .................. 356/37; 250/335; 73/28.02; 73/865.5
(58) Field of Classification Search ............. 356/37–38; 250/335

See application file for complete search history.

(56) References Cited

U.S. PATENT DOCUMENTS

| | | | | |
|---|---|---|---|---|
| 5,026,155 A | * | 6/1991 | Ockovic et al. ............... | 356/37 |
| 6,263,744 B1 | * | 7/2001 | Russell et al. ............... | 73/865.5 |
| 6,639,671 B1 | * | 10/2003 | Liu ........................... | 356/336 |
| 7,471,076 B2 | * | 12/2008 | Ahn .......................... | 324/71.4 |

\* cited by examiner

*Primary Examiner*—Gregory J Toatley, Jr.
*Assistant Examiner*—Rebecca C Slomski
(74) *Attorney, Agent, or Firm*—Lowe Hauptman Ham & Berner

(57) ABSTRACT

A particle measuring system and method is capable of separating particles on a size-by-size basis and measuring the number and size of the particles one by one on a real time basis. The particle measuring system includes a sampling device for guiding a stream of an aerosol containing particles suspended in a gas, an analysis device for separating one by one the particles contained in the aerosol, a filter for filtering out the particles contained in the aerosol to produce a filtered gas, a saturating device for saturating the filtered gas with working liquid to thereby produce a saturated gas, a condensing device for condensing the saturated gas to produce liquid droplets each having a nucleus formed of one of the particles, and an optical particle counter for calculating the number and size of the particles contained in the liquid droplets.

15 Claims, 3 Drawing Sheets

```
START
  ↓
SUPPLY AN AEROSOL CONTAINING POSITIVELY        — S100
AND NEGATIVELY CHARGED PARTICLES
  ↓
TAKE A SAMPLE AEROSOL AND
ALLOW THE REMAINING AEROSOL                    — S102
TO DIVERGE FROM THE SAMPLE AEROSOL
  ↓
FILTER OUT THE PARTICLES FROM
THE REMAINING AEROSOL TO                       — S104
PRODUCE A FILTERED GAS
  ↓
SATURATE THE FILTERED GAS WITH                 — S106
WORKING LIQUID TO PRODUCE A SATURATED GAS
  ↓
ALLOW THE SATURATED GAS TO JOIN                — S108
A STREAM OF THE SAMPLE AEROSOL
  ↓
SEPARATE THE POSITIVELY AND NEGATIVELY         — S110
CHARGED PARTICLES ON A SIZE-BY-SIZE BASIS
  ↓
CONDENSE THE SATURATED GAS TO PRODUCE
DROPLETS EACH HAVING A NUCLEUS FORMED OF       — S112
ONE OF THE PARTICLES
  ↓
DETECT THE LIQUID DROPLETS TO CACULATE         — S114
THE NUMBER AND SIZE OF THE PARTICLES
  ↓
END
```

PARTICLE MEASURING SYSTEM AND METHOD

CROSS REFERENCE

The present application is based on and claims priority from, Korean Application No. 10-2006-0065286, filed Jul. 12, 2006, the disclosure of which is hereby incorporated by reference herein in its entirety.

FIELD OF THE INVENTION

The present invention relates to a particle measuring system and method and, more particularly, to a particle measuring system and method capable of separating particles on a size-by-size basis and measuring the number and size of the particles one by one on a real time basis.

BACKGROUND OF THE INVENTION

An aerosol is defined as liquid or solid particles suspended in a gas and can be classified into smoke, dust, mist, fume and the like depending on the physical state of particles. The aerosol is detrimental to a human body and becomes a cause of pollution in various kinds of industries. For the purpose of accurate evaluation of the aerosol, collection and analysis of particles is becoming an important research subject.

Particles of the aerosol are measured by means of an optical particle counter (OPC) on a real time basis. Due to the scattering of a laser beam, the optical particle counter has no ability to accurately measure particles having a size of smaller than 60 nm. This means that the optical particle counter is not suitable for use in the fields requiring real time measurement of particles having a size of smaller than 60 nm, such as semiconductor production, medical chemistry, biology and genetic engineering.

A scanning mobility particle sizer (SMPS) is used in these fields to measure the aerosol on a real time basis. Particles of the aerosol are bipolar-charged by a neutralizer of the scanning mobility particle sizer and then supplied to a differential mobility analyzer (DMA). The differential mobility analyzer undergoes a change in voltage while the particles pass therethrough. The particles passing the differential mobility analyzer are affected by electric fields changing over time. Thus, those particles that have the same electrical mobility are extracted by the differential mobility analyzer.

The scanning mobility particle sizer has a condensation nucleus counter (CNC) designed to measure the number of particles while exponentially changing the voltage of the differential mobility analyzer over time. The number of particles thus measured is divided into particle numbers according to time intervals to thereby find particle concentrations relative to average electrical mobility in the respective time intervals. Particle size distributions are then found using a data on the particle concentrations.

However, the conventional scanning mobility particle sizer has a drawback in that it takes about two minutes to conduct the measurement once. This is because the scanning mobility particle sizer measures the particle size distribution based on the electrical mobility of the particles. Another shortcoming is that the scanning mobility particle sizer can be used only when the number of particles is as great as the number concentration in the atmosphere.

SUMMARY OF THE INVENTION

In view of the above-noted and other problems inherent in the prior art, it is an object of the present invention to provide a particle measuring system and method capable of separating particles on a size-by-size basis by use of electric mobility of the particles and measuring the number and size of the particles one by one on a real time basis.

Another object of the present invention is to provide a particle measuring system and method that can form liquid droplets each having a nucleus formed of one of the particles and can accurately measure the number and size of particles contained in the liquid droplets.

With these objects in view, one aspect of the present invention is directed to a particle measuring system, including: a sampling device for guiding a stream of an aerosol containing positively charged particles and negatively charged particles suspended in a gas, the sampling device adapted to take a part of the aerosol as a sample aerosol and also to allow the remaining part of the aerosol to diverge from the stream of the aerosol; an analysis device connected to the sampling device for guiding a stream of the sample aerosol, the analysis device designed to form an anode and a cathode along a flow direction of the sample aerosol to thereby separate the positively charged particles and the negatively charged particles on a size-by-size basis; a filter for filtering out the positively charged particles and the negatively charged particles contained in the remaining part of the aerosol to produce a filtered gas; a saturating device provided between the filter and the analysis device for guiding the filtered gas to the analysis device, the saturating device adapted to saturate the filtered gas with working liquid to thereby produce a saturated gas; a condensing device connected to the analysis device for condensing the saturated gas to produce liquid droplets each having a nucleus formed of one of the positively charged particles and the negatively charged particles; and an optical particle counter connected to the condensing device for detecting the liquid droplets supplied from the condensing device to thereby calculate the number and size of the positively charged particles and the negatively charged particles contained in the liquid droplets.

Another aspect of the present invention is directed to a particle measuring method, comprising the steps of: supplying an aerosol containing positively charged particles and negatively charged particles suspended in a gas; taking a part of the aerosol as a sample aerosol and allowing the remaining part of the aerosol to diverge from a stream of the sample aerosol; filtering out the positively charged particles and the negatively charged particles contained in the remaining part of the aerosol to produce a filtered gas; saturating the filtered gas with working liquid to produce a saturated gas; allowing the saturated gas to join the stream of the sample aerosol; forming an anode and a cathode along a flowing direction of the sample aerosol and the saturated gas to thereby separate one by one the positively charged particles and the negatively charged particles contained in the sample aerosol; condensing the saturated gas to produce liquid droplets each having a nucleus formed of one of the positively charged particles and the negatively charged particles; and detecting the liquid droplets by means of an optical particle counter to thereby calculate the number and size of the positively charged particles and the negatively charged particles contained in the liquid droplets.

BRIEF DESCRIPTION OF THE DRAWINGS

The above and other objects and features of the present invention will become apparent from the following description of a preferred embodiment, given in conjunction with the accompanying drawings, in which:

FIG. 1 is a section view showing a configuration of a particle measuring system in accordance with the present invention;

FIG. 4 is a flowchart for explaining a particle measuring method in accordance with the present invention.

DETAILED DESCRIPTION OF THE PREFERRED EMBODIMENTS

Figure 2:
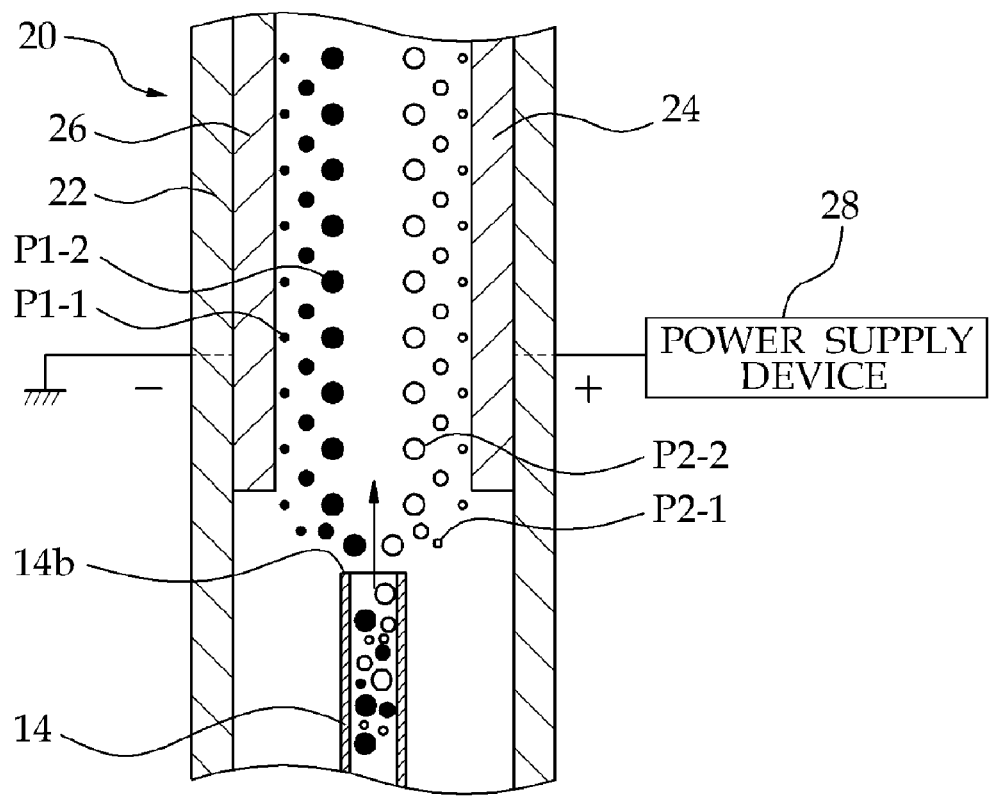
FIG. 2 is a section view illustrating an analysis device employed in the particle measuring system of the present invention.

A preferred embodiment of a particle measuring system and method in accordance with the present invention will now be described in detail with reference to the accompanying drawings.

Figure 1:
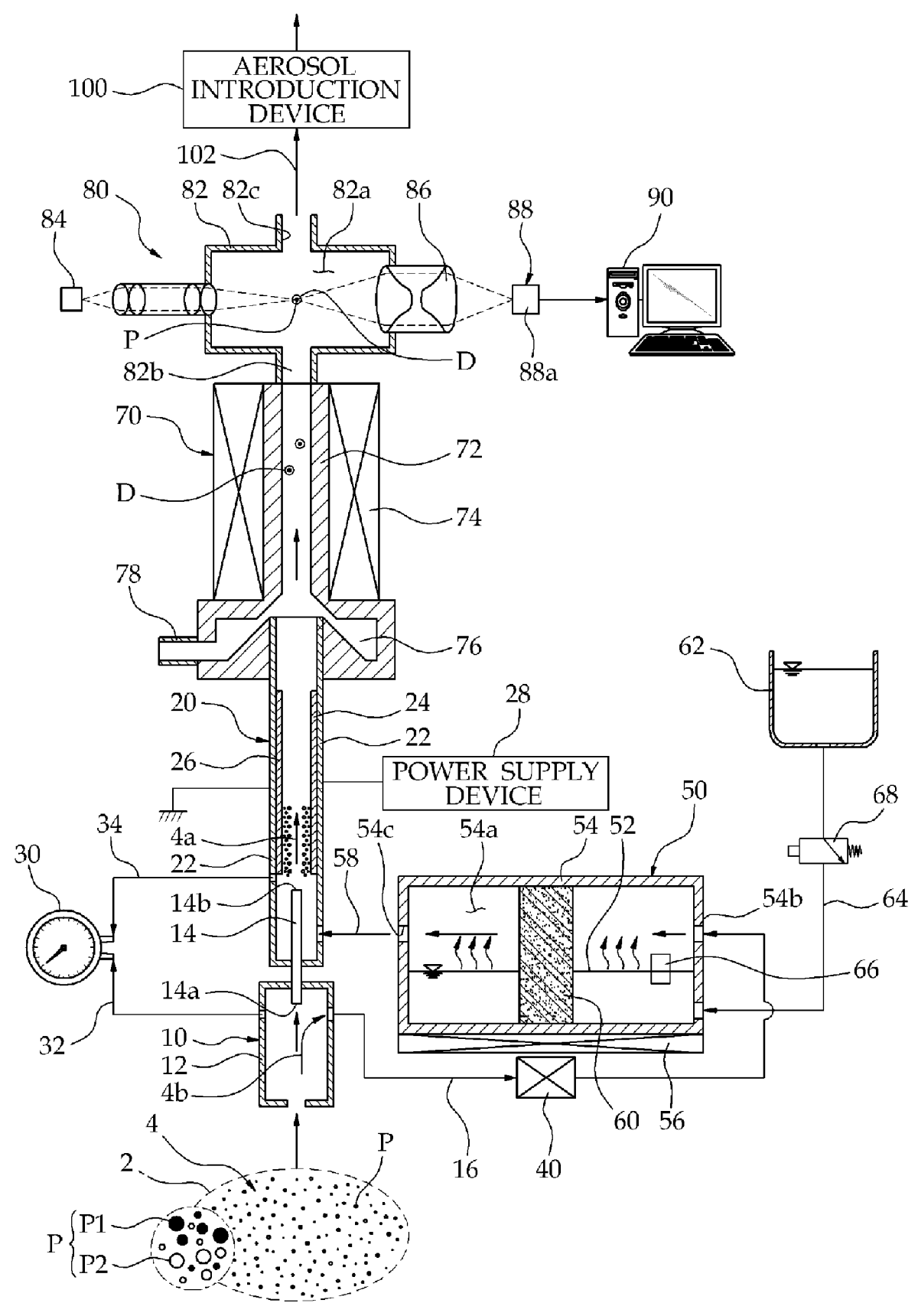

Referring first to FIG. 1, a particle measuring system of the present invention includes a sampling device 10 for sampling an aerosol 4 supplied from an aerosol source 2. The aerosol 4 supplied from an aerosol source 2 contains a large number of particles P suspended in a gas. The particles P are divided into positively charged particles P1 and negatively charged particles P2. These kinds of charged particles can be produced by conducting a bipolar charging operation in a neutralizer.

The sampling device 10 has a first duct 12 provided to guide a stream of the aerosol 4 supplied from the aerosol source 2. On a downstream side of the first duct 12, there is provided a sampling tube 14 having a reduced diameter. The sampling tube 14 has an inlet 14*a* protruding into the first duct 12 and an outlet 14*b* lying outside the first duct 12. The sampling tube 14 may be constructed from a capillary tube having an increased length and a reduced diameter. Alternatively, the sampling tube 14 may consist of a pinhole or a slit formed in a downstream portion of the first duct 12. A bypass pipe 16 for allowing a part of the aerosol 4 to diverge from the first duct 12 is connected to the first duct 12.

Referring to FIGS. 1 and 2, an analysis device 20 for analyzing the particles P contained in the aerosol 4 according to their electricity quantity and size is coupled to the outlet 14*b* of the sampling tube 14. The analysis device 20 includes a second duct 22 connected at its upstream end to the sampling tube 14 for guiding the stream of the aerosol 4, a first electrode 24 mounted to one side of an inner surface of the second duct 22, a second electrode 26 mounted to the other side of the inner surface of the second duct 22 and a power supply device 28 connected to one of the first electrode 24 and the second electrode 26 for supplying a positive voltage thereto. Although FIGS. 1 and 2 show that the first electrode 24 and the second electrode 26 are mounted to the inner surface of the second duct 22 in a mutually confronting relationship, they may be mounted to an outer surface of the second duct 22 if such a need exists. The power supply device 28 is connected to the first electrode 24 to supply a positive voltage thereto. The second electrode 26 remains electrically grounded. As an alternative, the second electrode 26 may not be grounded but connected to a power supply device so that it can be supplied with a negative voltage.

Referring again to FIG. 1, a differential manometer 30 is connected to the first duct 12 of the sampling device 10 and the second duct 22 of the analysis device 20. The differential manometer 30 has a first pipeline 32 connected to the first duct 12 and a second pipeline 34 connected to the second duct 22 on a downstream side of the outlet 14*a* of the sampling tube 14. The differential manometer 30 is operated to measure the pressure difference between the first duct 12 and the second duct 22. The pressure difference thus measured is used in controlling the flow rate of the aerosol 4.

Provided midway of the bypass pipe 16 of the sampling device 10 is a filter 40 that filters out the particles P in the aerosol 4 flowing through the bypass pipe 16. On the downstream side of the filter 40, there is provided a saturating device 50 for saturating the filtered gas, e.g., an air, with working liquid 52 to thereby generate saturated vapor. The saturating device 50 consists of a tank 54 for storing the working liquid 52 and a heater 56 attached to one side of the tank 54 for heating and evaporating the working liquid 52 stored in the tank 54.

The tank 54 has a chamber 54*a*, an inlet 54*b* connected to the bypass pipe 16 and an outlet 54*c* connected to an upstream portion of the second duct 22 of the analysis device 20 through a pipeline 58. The level of the working liquid 52 stored in the chamber 54*a* of the tank 54 is kept lower than the inlet 54*b* and the outlet 54*c*. Water, alcohol or the like is used as the working liquid 52. A porous member 60 is installed within the chamber 54*a* of the tank 54. The porous member 60 is immersed at its lower portion into the working liquid 52 and exposed at its upper portion to a gas flowing through the chamber 54*a*. The porous member 60 soaks up the working liquid 52 by a capillary phenomenon.

A reservoir 62 is connected to the chamber 54*a* of the tank 54 via a pipeline 64 so that it can supply the working liquid 52 to the chamber 54*a*. A level sensor 66 for detecting the level of the working liquid 52 is provided within the chamber 54*a* of the tank 54 and an electromagnetic valve 68 for controlling the flow of the working liquid 52 in response to a signal generated by the level sensor 66 is installed on the pipeline 64.

A condensing device 70 includes a third duct 72 connected to the second duct 22 of the analysis device 20 and a thermoelectric cooler 74 attached to an outer surface of the third duct 72, the thermoelectric cooler 74 adapted to serve as a cooling means for lowering the temperature of the third duct 72. The cooling means may consist of a cooling chamber enclosing the outer surface of the third duct 72 and a cooling unit having a cooling cycle by which coolant is supplied to the cooling chamber to reduce the temperature of the third duct 72.

Referring to FIGS. 1 and 3, a saturated gas is introduced into the third duct 72 of the condensing device 70 and then supersaturated as a result of temperature reduction. The supersaturated gas is condensed in the condensing device 70. More specifically, the saturated gas is condensed into liquid droplets D each having a nucleus formed of one of the particles P. The liquid droplets D is borne by a gas stream to the outside of the third duct 72. A drain pan 76 for gathering the condensed liquid discharged from the third duct 72 is provided in the lower end portion of the third duct 72 and a drainpipe 78 for draining the condensed liquid is connected to the drain pan 76.

The particle measuring system of the present invention includes a optical particle counter (OPC) 80 for optically counting the liquid droplets D supplied from the third duct 72 of the condensing device 70 to thereby calculate the number and size of the particles P. The optical particle counter 80 consists of a housing 82, a light source 84, a lens 86, a photo detector 88 and a computer 90.

The housing 82 has a sensing space 82*a*, an inlet 82*b* and an outlet 82*c*. The inlet 82*b* of the housing 82 is connected to the third duct 72 of the condensing device 70. The light source 84 is arranged on one side of the housing 82 to irradiate light into the sensing space 82*a* of the housing 82. The lens 86 is arranged on the other side of the housing 82 to collect the light irradiated from the light source 84. The photo detector 88 detects the light collected by the lens 86 and issues signals corresponding thereto. The signals of the photo detector 88 are inputted to the computer 90 which in turn processes the signals with a pre-stored program to calculate the number and size of the particles P, i.e., the nuclei of the liquid droplets D. In order to acquire an image data of the liquid droplets D, the photo detector 88 consists of an image sensor 88a, examples of which include a charge coupled device camera and a quadrature detector. The computer 90 may consist of a signal processor for processing the signals of the photo detector 88 to calculate and output the number and size of the particles P.

An aerosol introduction device 100 for generating a suction force to draw the aerosol 4 into the first duct 12 of the sampling device 10 is connected to the outlet 82c of the housing 82 through a pipeline 102. The aerosol introduction device 100 may consist of a blower or a vacuum pump for forcibly sucking and discharging the aerosol 4 and a mass flow controller for controlling the flow rate of the aerosol 4. If necessary, the aerosol introduction device 100 may be installed on the upstream side of the first duct 12.

Now, a particle measuring method of the present invention performed by the particle measuring system as configured above will be described with reference to FIG. 4.

Referring collectively to FIGS. 1 and 4, the aerosol introduction device 100 is operated to introduce the aerosol 4, which contains positively and negatively charged particles suspended in a gas, into the first duct 12 of the sampling device 10 (step S100). As a suction force is generated by the aerosol introduction device 100, the aerosol 4 is supplied from the aerosol source 2 to the first duct 12 of the sampling device 10.

A part of the aerosol 4 thus supplied is taken as a sample aerosol by means of the sampling device 10 and the remaining part of the aerosol 4 is diverged from the main stream of the aerosol 4 (step S102). More specifically, a part of the aerosol 4 supplied to the first duct 12 of the sampling device 10 is fed, as a sample aerosol 4a, to the second duct 22 of the analysis device 20 through the sampling tube 14. The remaining aerosol 4b is diverged from the main stream of the aerosol 4 and discharged from the first duct 12 through the bypass pipe 16.

The particles P contained in the aerosol 4b flowing through the bypass pipe 16 are filtered out by means of the filter 40 (step S104). The filtered gas is saturated with the working liquid 52 to produce a saturated gas (step S106). The saturated gas is supplied to the second duct 22 of the analysis device 20 so that it can join the stream of the sample aerosol 4a (step S108). More specifically, the gas going through the filtering in the filter 40 is introduced into the chamber 54a through the inlet 54b of the tank 54. The tank 54 is heated by the heater 56, as a result of which the working liquid 52 stored in the tank 54 is evaporated. In order to accelerate the evaporation of the working liquid 52, the heater 56 applies heat to the tank 54 so that the temperature within the chamber 54a can be kept 30 to 35° C. higher than the temperature around the tank 54. The gas flowing through the chamber 54a of the tank 54 is saturated with the evaporated working liquid 52 into a saturated gas. The saturated gas is supplied to the second duct 22 of the analysis device 20 through the pipeline 58, thereby joining the stream of the sample aerosol 4a.

The porous member 60 received within the chamber 54a of the tank 54 soaks up the working liquid 52 at its lower portion, while the gas flowing through the chamber 54a of the tank 54 makes contact with the upper portion of the porous member 60. By allowing the gas to make contact with the porous member 60 soaked with the working liquid 52 in this way, the contact area between the gas and the porous member 60 is increased to thereby accelerate the saturation of the gas by the working liquid 52.

Referring to FIG. 2, as the sample aerosol 4a is supplied to the second duct 22 of the analysis device 20, the power supply device 28 is operated to apply a positive voltage to the first electrode 24 so that an anode and a cathode can be formed on the opposite sides of the sample aerosol 4a flowing through the second duct 22. By doing so, the particles P in the sample aerosol 4a are separated on a size-by-size basis (step S110).

If the positive voltage is applied to the first electrode 24 by means of the power supply device 28, the first electrode 24 acts as an anode and the second electrode 26 kept grounded serves as a cathode. Thus, the positively charged particles P1 move toward the second electrode 26 and the negatively charged particles P2 move toward the first electrode 24. The velocity at which the positively charged particles P1 and the negatively charged particles P2 are moved toward the first and second electrodes 24 and 26 vary with the size thereof. In other words, the positively and negatively charged particles P1-1 and P2-1 having a relatively small size are moved faster than the positively and negatively charged particles P1-2 and P2-2 having a relatively great size.

In this way, the positively charged particles P1 and the negatively charged particles P2 are moved toward the first electrode 24 and the second electrode 26 and then discharged to the outside of the second duct 22 together with the stream of the saturated gas flowing through the second duct 22. As a result, when discharged to the outside of the second duct 22, the positively charged particles P1 and the negatively charged particles P2 are aligned in specified positions depending on the size thereof. In other words, when discharged to the outside of the second duct 22, the negatively charged particles P2-1 having a relatively small size are positioned near to the first electrode 24 but the negatively charged particles P2-2 having a relatively great size are positioned farther form the first electrode 24 than the negatively charged particles P2-1 having a relatively small size are. This holds true for the positively charged particles P1-1 having a relatively small size and the positively charged particles P1-2 having a relatively great size.

Figure 3:
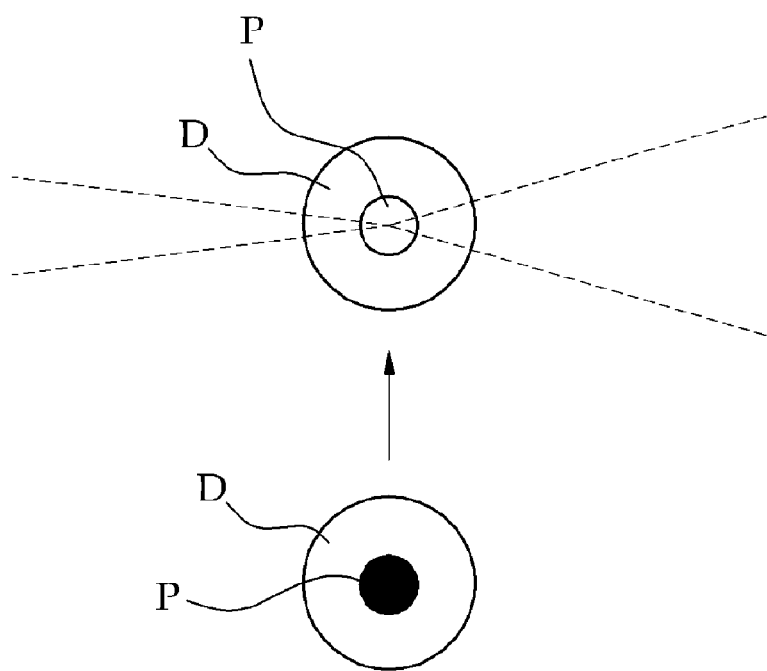
FIG. 3 is a view microscopically illustrating a liquid droplet produced by the particle measuring system of the present invention, the liquid droplet having a nucleus formed of one of particles.

The saturated gas is condensed to produce liquid droplets D, each of which has a nucleus formed of one of the particles P dispersed in the sample aerosol 4a (step S112). More specifically, the sample aerosol 4a and the saturated gas are discharged from the second duct 22 of the analysis device 20 and then supplied to the third duct 72 of the condensing device 70. If the temperature of the third duct 72 is reduced to, e.g., 10° C., by means of the thermoelectric cooler 74, the saturated gas is turned to a supersaturated gas. As shown in FIG. 3, the gas is condensed to build up liquid droplets D, each of which has a nucleus formed of one of the particles P dispersed in the supersaturated gas. The liquid droplets D thus built up have a size proportional to the size of the particles P. For example, a liquid droplet having a nucleus formed of a 10 nm particle grows to have a size of about 10 μm which is nearly 1000 times as great as the size of the particle. During condensation of the saturated gas, a condensed liquid is produced on the inner surface of the third duct 72. The condensed liquid flows downwardly along the inner surface of the third duct 72 and gathered in the drain pan 76. Thereafter, the condensed liquid is discharged from the drain pan 76 to the outside through the drainpipe 78.

Referring to FIGS. 1 and 3, the optical particle counter 80 is operated to detect the liquid droplets D and to calculate the number and size of the particles P contained in the respective liquid droplets D (step S114). More specifically, the liquid droplets D leaving the second duct 22 of the analysis device 20 are introduced into the sensing space 82a through the inlet 82b of the housing 82 and subsequently discharged from the sensing space 82a to the outside of the housing 82 through the outlet 82c. In this process, the light source 84 is operated to irradiate light toward the sensing space 82a, which light is scattered by the liquid droplets D moving through the sensing space 82a. The light thus scattered is collected by the lens 86 and then sent to the photo detector 88 which in turn detects the scattered light and outputs signals corresponding thereto. The computer 90 calculates the number and size of the particles P by processing the signals inputted from the photo detector 88 with a pre-stored program. Finally, the computer 90 allows a monitor or other display devices to display the number and size of the particles P thus calculated. The particles P and the liquid droplets D discharged from the particle measuring system is filtered and removed by means of a filtering device.

As described hereinabove, the particle measuring system and method in accordance with the present invention is adapted to separate particles on the size-by-size basis by use of electric mobility of the particles and then to produce liquid droplets each having a nucleus formed of one of positively and negatively charged particles. By detecting the liquid droplets, it becomes possible to accurately measure the number and size of the particles one by one on a real time basis.

The embodiments set forth hereinabove have been presented for illustrative purpose only and, therefore, the present invention is not limited to these embodiments. It will be understood by those skilled in the art that various changes and modifications may be made without departing from the scope of the invention defined in the claims.

What is claimed is:

1. A particle measuring system, comprising:
   a sampling device for guiding a stream of an aerosol containing positively charged particles and negatively charged particles suspended in a gas, the sampling device adapted to take a part of the aerosol as a sample aerosol and also to allow the remaining part of the aerosol to diverge from the stream of the aerosol;
   an analysis device connected to the sampling device for guiding a stream of the sample aerosol, the analysis device designed to form an anode and a cathode along a flow direction of the sample aerosol to thereby separate the positively charged particles and the negatively charged particles on a size-by-size basis;
   a filter for filtering out the positively charged particles and the negatively charged particles contained in the remaining part of the aerosol to produce a filtered gas;
   a saturating device provided between the filter and the analysis device for guiding the filtered gas to the analysis device, the saturating device adapted to saturate the filtered gas with working liquid to thereby produce a saturated gas;
   a condensing device connected to the analysis device for condensing the saturated gas to produce liquid droplets each having a nucleus formed of one of the positively charged particles and the negatively charged particles; and
   an optical particle counter connected to the condensing device for detecting the liquid droplets supplied from the condensing device to thereby calculate the number and size of the positively charged particles and the negatively charged particles contained in the liquid droplets.

2. The particle measuring system as recited in claim 1, wherein the sampling device comprises:
   a first duct for guiding the stream of the aerosol;
   a sampling tube attached to a downstream side of the first duct for guiding the stream of the sample aerosol, the analysis device connected to a downstream side of the sampling tube; and
   a bypass pipe connected to the first duct to guide a stream of the remaining part of the aerosol diverging from the first duct, the filter attached to a downstream side of the bypass pipe.

3. The particle measuring system as recited in claim 1, wherein the analysis device comprises:
   a second duct connected at an upstream end to the sampling device and the saturating device for guiding the stream of the sample aerosol and the saturated gas;
   a first electrode attached to one side of the second duct;
   a second electrode attached to the other side of the second duct in a confronting relationship with the first electrode; and
   a power supply device for applying a positive voltage to one of the first electrode and the second electrode, wherein the other of the first electrode and the second electrode is kept electrically grounded.

4. The particle measuring system as recited in claim 3, wherein a differential manometer for measuring a pressure difference between the sampling device and the analysis device is connected to the sampling device and the analysis device through a first pipeline and a second pipeline.

5. The particle measuring system as recited in claim 1, wherein the saturating device comprises:
   a tank having a chamber connected to a downstream side of the filer and an upstream side of the analysis device, the tank storing the working liquid in such a way that the filtered gas can flow through the chamber; and
   a heater attached to one side of the tank for heating the tank to evaporate the working liquid.

6. The particle measuring system as recited in claim 5, wherein the saturating device further comprises:
   a porous member provided within the tank, the porous member immersed at a lower portion in the working liquid to soak up the working liquid and exposed out of the working liquid at an upper portion to make contact with the filtered gas.

7. The particle measuring system as recited in claim 5, wherein the saturating device further comprises:
   a reservoir connected to the tank through a supply pipeline for supplying the working liquid to the chamber of the tank;
   a level sensor provided within the chamber of the tank for detecting the level of the working liquid; and
   an electromagnetic valve attached to the supply pipeline for controlling a flow rate of the working liquid in response to a signal from the level sensor.

8. The particle measuring system as recited in claim 1, wherein the condensing device comprises:
   a third duct connected to a downstream side of the analysis device for guiding a stream of the saturated gas; and
   a cooler attached to an outer surface of the third duct for reducing a temperature of the third duct to thereby condense the saturated gas.

9. The particle measuring system as recited in claim 8, wherein the cooler comprises a thermoelectric element and wherein a drain pan for gathering a condensed liquid discharged from the third duct is provided below the third duct, the drain pan having a drainpipe through which the condensed liquid is drained to the outside.

10. The particle measuring system as recited in claim 1, wherein the optical particle counter comprises:

a housing connected to a downstream side of the condensing device for guiding a stream of the liquid droplets, the housing having a sensing space;

a light source arranged on one side of the housing for irradiating light toward the liquid droplets moving through the sensing space of the housing;

a photo detector arranged on the other side of the housing for detecting the light irradiated from the light source to thereby generate light detection signals; and a computer for processing the signals supplied from the photo detector to thereby calculate the number and size of the particles.

11. The particle measuring system as recited in claim 10, wherein the photo detector is comprised of an image sensor for acquiring an image data of the liquid droplets.

12. The particle measuring system as recited in claim 10, further comprising an aerosol introduction device connected to the housing of the optical particle counter for generating a suction force to draw the aerosol into the sampling device.

13. A particle measuring method, comprising the steps of:
supplying an aerosol containing positively charged particles and negatively charged particles suspended in a gas;

taking a part of the aerosol as a sample aerosol and allowing the remaining part of the aerosol to diverge from a stream of the sample aerosol;

filtering out the positively charged particles and the negatively charged particles contained in the remaining part of the aerosol to produce a filtered gas;

saturating the filtered gas with working liquid to produce a saturated gas;

allowing the saturated gas to join the stream of the sample aerosol;

forming an anode and a cathode along a flowing direction of the sample aerosol and the saturated gas to thereby separate the positively charged particles and the negatively charged particles on a size-by-size basis;

condensing the saturated gas to produce liquid droplets each having a nucleus formed of one of the positively charged particles and the negatively charged particles; and detecting the liquid droplets by means of an optical particle counter to thereby calculate the number and size of the positively charged particles and the negatively charged particles contained in the liquid droplets.

14. The particle measuring method as recited in claim 13, wherein the step of saturating the filtered gas comprises storing the working liquid in a chamber of a tank, allowing the filtered gas to flow through the chamber of the tank and heating the tank to evaporate the working liquid.

15. The particle measuring method as recited in claim 14, wherein the step of saturating the filtered gas further comprises allowing the filtered gas to make contact with a porous member soaked with the working liquid.

* * * * *